(12) United States Patent
Matsui et al.

(10) Patent No.: US 9,393,191 B2
(45) Date of Patent: Jul. 19, 2016

(54) PICEATANNOL-CONTAINING COMPOSITION AND METHOD OF PRODUCING PICEATANNOL-CONTAINING COMPOSITION

(71) Applicant: MORINAGA & CO. LTD., Tokyo (JP)

(72) Inventors: Yuko Matsui, Yokohama (JP); Masanori Kamei, Yokohama (JP); Kenkichi Sugiyama, Yokohama (JP)

(73) Assignee: MORINAGA & CO., LTD., Tokyo (JP)

( * ) Notice: Subject to any disclaimer, the term of this patent is extended or adjusted under 35 U.S.C. 154(b) by 410 days.

(21) Appl. No.: 13/719,841

(22) Filed: Dec. 19, 2012

(65) Prior Publication Data
US 2013/0165529 A1 Jun. 27, 2013

Related U.S. Application Data

(62) Division of application No. 13/256,552, filed as application No. PCT/JP2009/056945 on Apr. 3, 2009, now Pat. No. 8,617,620.

(51) Int. Cl.
| | | |
|---|---|---|
| *A61K 36/00* | (2006.01) | |
| *A61K 8/97* | (2006.01) | |
| *A61K 31/05* | (2006.01) | |
| *A23L 1/30* | (2006.01) | |
| *A61K 8/34* | (2006.01) | |
| *A61K 36/185* | (2006.01) | |
| *A61Q 19/02* | (2006.01) | |
| *C07C 37/82* | (2006.01) | |

(52) U.S. Cl.
CPC ................ *A61K 8/97* (2013.01); *A23L 1/3002* (2013.01); *A61K 8/347* (2013.01); *A61K 31/05* (2013.01); *A61K 36/185* (2013.01); *A61Q 19/02* (2013.01); *C07C 37/82* (2013.01)

(58) Field of Classification Search
None
See application file for complete search history.

(56) References Cited

U.S. PATENT DOCUMENTS

| 2006/0134244 A1 | 6/2006 | Takemoto |
| 2008/0118449 A1 | 5/2008 | Ronlan |

FOREIGN PATENT DOCUMENTS

| CN | 1710043 A | 12/2005 |
| DE | 42 38 509 A1 | 5/1994 |
| JP | 2005-075766 | 3/2005 |
| JP | 2005-281179 | 10/2005 |
| JP | 2007-302659 | 11/2007 |
| JP | 2007-531734 | 11/2007 |
| JP | 2009-13159 | 1/2009 |
| WO | 2005/012507 A1 | 2/2005 |
| WO | 2005/023740 A2 | 3/2005 |
| WO | 2008/086400 | 7/2008 |

OTHER PUBLICATIONS

Matsui et al, Effect of passion fruit on skin health. Acta Horticulturae (2009), 841(Proceedings of the IInd International Symposium on Human Health Effects of Fruits and Vegetables, 2007), 557-561.*
Po-Lin Kuo and Ya-Ling Hsu, "The grape and wine constituent piceatannol inhibits proliferation of human bladder cancer cells via blocking cell cycle progression and inducing Fas/membrane bound Fas ligand-mediated apoptotic pathway", Molecular Nutrition & Food Research, 2008, 52, pp. 408-418.
Extended European Search Report for Application No. EP 09 84 2669 dated Jul. 11, 2012.
Correa N C F, et al., "Extraction of passion fruit (Passiflora edulis) seed oil with supercritical C02", Database FSTA, International Food Information Service, XP002678584, Database accession No. FS-1995-11-N-0029, vol. 14, no. suppl., 1994, p. 29.
Agnes M. Rimando, et al., "Resveratrol, Pterostilbene, and Piceatannol in Vaccinium Berries", Journal of Agricultural and Food Chemistry, vol. 52, No. 15, 2004, pp. 4713-4719, XP002678585.
Bavaresco L, et al., "The occurrence of the stilbene piceatannol in grapes", Database FSTA, International Food Information Service, XP002678586, Database accession No. FS-2003-02-Hj0458, vol. 41, No. 3, 2002, p. 133.
Alane Cabral de Oliveira, et al., "Total phenolic content and free radical scavenging activities of methanolic extract powders of tropical fruit residues", Food Chemistry, Elsevier Ltd., vol. 115, No. 2, 2009, pp. 469-475, XP026002719.
International Search Report for International Application No. PCT/JP2009/056945 mailed Apr. 28, 2009.
"Endothelin-1 synthesis reduced by red wine", Nature, 2001, vol. 414, pp. 863 and 864.
Saburi A. Adesanya, et al., "Stilbene Derivatives from Cissus quadrangularis", Journal of Natural Products, 1999, vol. 62, pp. 1694 and 1695.
Takao Yokozawa, et al., "Piceatannol Inhibits Melanogenesis by Its Antioxidative Actions", Biological & Pharmaceutical Bulletin, 2007, vol. 30, No. 11, pp. 2007-2011.
Liu et al, Optimization of process parameters for supercritical carbon dioxide extraction of Passiflora seed oil by response surface methodology, Journal of Supercritical fluids (2009), 48 (1), 9-14.

* cited by examiner

*Primary Examiner* — Qiuwen Mi
(74) *Attorney, Agent, or Firm* — Smith, Gambrell & Russell, LLP.

(57) ABSTRACT

Provided are a piceatannol-containing composition which is a composition originating in a natural material and containing piceatannol at a high concentration, and a method of producing the piceatannol-containing composition. A piceatannol-containing composition which contains 0.0001 to 99.9% by mass of piceatannol is obtained by extracting passion fruit seeds. The extraction of piceatannol is carried out by grinding the passion fruit seeds, adding at least one solvent selected from an aqueous alcohol-based solvent and an aqueous ketone-based solvent and agitating to thereby extract piceatannol into the above-described solvent. In this case, it is preferable to conduct stepwise extraction by using both of the aqueous alcohol-based solvent and the aqueous ketone-based solvent.

4 Claims, 5 Drawing Sheets

PICEATANNOL-CONTAINING COMPOSITION AND METHOD OF PRODUCING PICEATANNOL-CONTAINING COMPOSITION

CROSS REFERENCE TO RELATED APPLICATION

This application is a division of Ser. No. 13/256,552 filed on Sep. 14, 2011, which is a 371 National Phase of PCT/JP2009/056945, filed Apr. 3, 2009, which all are being incorporated in their entirety herein by reference.

TECHNICAL FIELD

The present invention relates to a piceatannol-containing composition, which contains piceatannol derived from a passion fruit seed, and a method of producing a piceatannol-containing composition.

BACKGROUND ART

Non Patent Literature 1 below describes that resveratrol and piceatannol, which are polyphenol compounds derived from grape, have effects of inhibiting melanin production by melanin-producing cells. However, to perform a test for confirming the effects, a commercially available reagent is used, and the literature does not describe that a composition containing piceatannol or the like derived from a natural material such as grape is obtained.

Meanwhile, Patent Literature 1 below describes that resveratrol is concentrated and collected inexpensively, selectively, and efficiently from an extract of roots of *Reynoutria japonica* Houtt. var. *japnica*. Further, Patent Literature 2 below describes a cowberry extract containing resveratrol. Still further, Patent Literatures 3 and 4 below describe an extract of passion fruit (Passifloraceae, *Passiflora* sp.), in particular, an extract of passion fruit pericarp and use of the extract in foods, dietary supplements, and medical fields.

However, none of the arts described in the above-mentioned literatures provides a composition, which is obtained from a natural material and contains piceatannol at a high content.

CITATION LIST

Patent Literature

[PTL 1] JP 2005-281179 A
[PTL 2] JP 2009-13159 A
[PTL 3] JP 2007-302659 A
[PTL 4] JP 2007-531734 A

Non Patent Literature

[NPL 1] Takako Yokozawa and You Jung Kim, Piceatannol Inhibits Melanogenesis by Its Antioxidative Actions, Biological & Pharmaceutical Bulletin Vol. 30 (2007) No. 11 p 2007-2011

SUMMARY OF INVENTION

Technical Problem

From a general viewpoint of food safety, piceatannol to be blended in a food or beverage such as a functional food or a health food is preferably derived from a natural material. However, hitherto, a natural material containing piceatannol at a high content is not n known. Natural materials such as grapes contain piceatannol at a very low content.

Therefore, the object of the present invention is to provide a piceatannol-containing composition, which is derived from a natural material and contains piceatannol at a high content, and a method of producing a piceatannol-containing composition.

Solution to Problem

The inventors of the present invention have made intensive studies to achieve the above-mentioned object. As a result, the inventors have found that passion fruit seed, which the applications were not found since it has been discarded heretofore, contains piceatannol at a high content, thus completing the present invention.

That is, a piceatannol-containing composition of the present invention is obtained from a passion fruit seed and contains piceatannol at a content of 0.0001 to 99.9 mass %.

According to the piceatannol-containing composition of the present invention, it is possible to provide a composition, which is derived from a natural material and contains piceatannol at a high content. The composition is derived from a natural material and is hence suitably blended in a cosmetic, a drug, and a food or beverage such as a functional food or a health food.

Meanwhile, a method of producing a piceatannol-containing composition according to the present invention includes: pulverizing the passion fruit seed; adding at least one kind of a selected aqueous alcohol-based solvent and an aqueous ketone-based solvent; and stirring the mixture to extract piceatannol into the solvent.

According to the method of producing a piceatannol-containing composition according to the present invention, a composition, which is derived from a natural material that contains piceatannol at a high content, can be produced at a high yield because piceatannol is extracted from a passion fruit seed using an aqueous alcohol-based solvent or an aqueous ketone-based solvent.

The method of producing a piceatannol-containing composition according to the present invention preferably includes: pulverizing a passion fruit seed; adding any one of an aqueous alcohol-based solvent and an aqueous ketone-based solvent; stirring the mixture to extract piceatannol into the solvent, thereby obtaining a first extract; adding the other not selected in the above out of the aqueous alcohol-based solvent and the aqueous ketone-based solvent to the residue not collected as the extract; stirring the mixture to extract piceatannol into the solvent, thereby obtaining a second extract; and mixing the first extract and the second extract. According to this embodiment, a piceatannol-containing composition, which contains piceatannol at a high content, can be produced at a higher yield because extraction is performed in a stepwise manner with a plurality of solvents.

In the method of producing a piceatannol-containing composition according to the present invention, the passion fruit seed is preferably a raw passion fruit seed or a dried passion fruit seed, which is obtained by drying the raw passion fruit seed.

Further, in the method of producing a piceatannol-containing composition according to the present invention, the aqueous alcohol-based solvent is preferably aqueous ethanol, or the aqueous ketone-based solvent is preferably aqueous acetone. With regard to the water contents, the aqueous ethanol preferably contains 20 to 99.9 vol % of ethanol, and the aqueous acetone preferably contains 20 to 99.9 vol % of acetone. According to those embodiments, higher piceatannol extraction efficiency is provided.

In the method of producing a piceatannol-containing composition according to the present invention, the stirring in each of the solvents is preferably performed by ultrasonic vibration or shaking. According to this embodiment, higher piceatannol extraction efficiency is provided.

Further, the method of producing a piceatannol-containing composition according to the present invention preferably further includes distilling off the solvent under reduced pressure after the extraction.

Meanwhile, another embodiment of the present invention is a food or beverage, having added thereto a piceatannol-containing composition, which is obtained from a passion fruit seed and contains piceatannol at a content of 0.0001 to 99.9 mass %.

Further, still another embodiment of the present invention is a cosmetic, having added thereto a piceatannol-containing composition, which is obtained from a passion fruit seed and contains piceatannol at a content of 0.0001 to 99.9 mass %.

Advantageous Effects of Invention

According to the piceatannol-containing composition of the present invention, it is possible to provide a composition, which is derived from a natural material and contains piceatannol at a high content. The composition is derived from a natural material and hence is suitably blended in a cosmetic, a drug, and a food or beverage such as a functional food or a health food. Meanwhile, according to the method of producing a piceatannol-containing composition according to the present invention, a composition, which is derived from a natural material and contains piceatannol at a high content, can be produced at a high yield because an aqueous alcohol-based solvent or an aqueous ketone-based solvent is used as a solvent for extracting piceatannol from passion fruit seed. Moreover, the extraction may be performed in a stepwise manner with a plurality of solvents each belonging to the aqueous alcohol-based solvent or the aqueous ketone-based solvent, to thereby producing the composition at a higher yield.

DESCRIPTION OF EMBODIMENTS

Figure 1A:
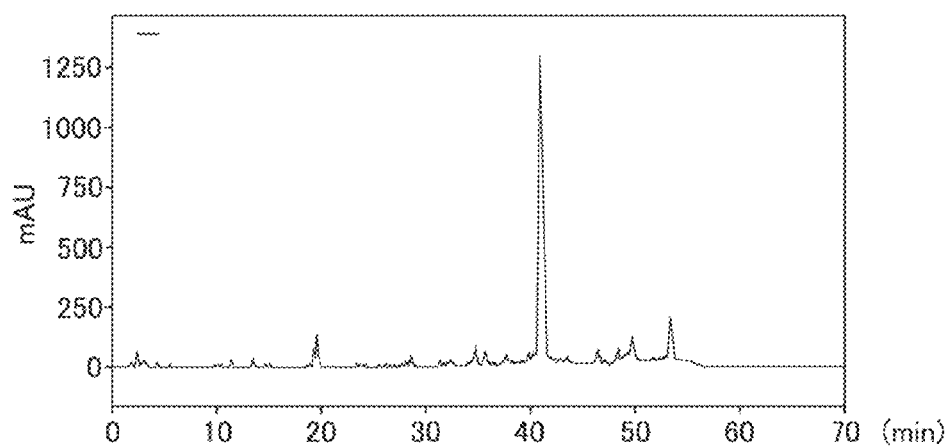
FIG. 1 Diagrams showing HPLC chromatograms of extracts from seeds (A), pericarp (b), and sarcocarp (C).

The piceatannol-containing composition of the present invention is a composition, which is obtained from passion fruit seeds and contains piceatannol at a content of 0.0001 to 99.9 mass %. The composition may have a liquid, solid, semisolid, or gel form, for example, and may be passion fruit seeds per se or a processed seed product such as a paste obtained by pulverizing the seeds or powder obtained by pulverizing a freeze-dried product of the seeds. The content of piceatannol in terms of solid content is preferably 0.0001 to 99.9 mass %, more preferably 0.01 to 50 mass %, most preferably 0.1 to 10 mass %.

Piceatannol is represented by the following chemical formula (1).

[Chem. 1]

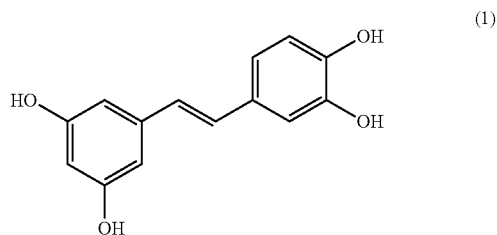

Piceatannol represented by the above-mentioned chemical formula is trans-piceatannol having a structure in which two phenyl groups are linked through a trans-alkene group, but in the present invention, piceatannol also includes cis-piceatannol having a structure in which two phenyl groups are linked through a cis-alkene group in the above-mentioned chemical formula.

Passion fruit is a plant belonging to the family Passifloraceae of the genus *Passiflora* and is also called Kudamonotokeisou, and the fruit has a sweet-sour taste and is eaten as a fruit without treatments, is drunk as a juice, or is used as a flavor to blend in a food or beverage such as jelly or cake. Seeds of the passion fruit are hard and they are removed from the fruit when processed to juice or the like, and even if the fruit is eaten or drunk with the seeds, the seeds are excreted because the seeds have hard hulls and are difficult to digest. The present invention is based on the finding that the passion fruit seeds, which have not found applications and hence have been discarded heretofore, contain piceatannol at a high content. It should be noted that if the passion fruit seeds used in the present invention are blended in a food or beverage such as a functional food or a health food, there is no problem in safety, as supported by previous experiences of eating the passion fruit.

Preferably, the piceatannol-containing composition of the present invention can be obtained by, for example, a method including pulverizing raw or dried passion fruit seeds and performing extraction using a solvent out of a variety of solvents. In order to increase extraction efficiency, the passion fruit seeds may be appropriately subjected to a chemical treatment such as acid or alkaline decomposition or enzymatic decomposition before extraction. Moreover, according to the method of producing a piceatannol-containing composition according to the present invention as described below, a composition containing piceatannol at a high content can be obtained at a particularly high yield, and hence the composition is most preferably obtained by the method.

Hereinafter, the method of producing a piceatannol-containing composition according to the present invention is described.

In the method of producing a piceatannol-containing composition according to the present invention, first, the passion fruit seeds are pulverized. The passion fruit seeds to be used may be raw or dried passion fruit seeds, and in order to increase the extraction efficiency, the chemical treatment such as acid or alkaline decomposition or enzymatic decomposition may be appropriately performed before extraction. Pulverization may be performed using a known pulverizer. It should be noted that the passion fruit seeds have a high oil content, and hence the seeds may become paste-like after pulverization.

Subsequently, at least one kind selected from an aqueous alcohol-based solvent and an aqueous ketone-based solvent is added to the pulverized passion fruit seeds, and the mixture was stirred to extract piceatannol into the solvent.

The aqueous alcohol-based solvent which may be used includes aqueous solvents such as aqueous ethanol, aqueous methanol, and aqueous propanol, and aqueous ethanol is particularly preferred. Meanwhile, the aqueous ketone-based solvent which may be used includes aqueous solvents such as aqueous acetone, aqueous methyl ethyl ketone, aqueous diethyl ketone, and aqueous chloroacetone, and aqueous acetone is particularly preferred.

With regard to the water contents, the aqueous ethanol contains preferably 20 to 99.9 vol % of ethanol, more preferably 40 to 99.9 vol % of ethanol, most preferably 60 to 80 vol % of ethanol, and the aqueous acetone contains preferably 20 to 99.9 vol % of acetone, more preferably 40 to 99.9 vol % of acetone, most preferably 60 to 80 vol % of acetone. If the contents do not fall within the above-mentioned ranges, the extraction efficiency of piceatannol may deteriorate, which is not preferred. It should be noted that, to simplify the notations of the water contents of the aqueous solvents, for example, 80 vol % ethanol containing 20 vol % water is referred to as "80% aqueous ethanol." Moreover, for example, 70 vol % ethanol containing 30 vol % water is referred to as "70% aqueous ethanol." Further, for example, 70 vol % acetone containing 30 vol % water is referred to as "70% aqueous acetone."

In the method of producing a piceatannol-containing composition according to the present invention, the stirring in each of the above-mentioned solvents is preferably performed by ultrasonic vibration or shaking. This can give vibrations effectively to the passion fruit seeds pulverized and contacted with each of the above-mentioned solvents, and hence it is possible to increase the extraction efficiency of piceatannol from the passion fruit seeds into each of the above-mentioned solvents. The ultrasonic vibration can be given by a known ultrasonic device. The shaking can be given by a known shaking device.

Further, in the method of producing a piceatannol-containing composition according to the present invention, the above-mentioned solvents are preferably distilled off under reduced pressure after the extraction. This can produce a composition containing no organic solvent, which can comply with safety standards and the like of a food material to be blended in a food or beverage such as a functional food or a health food.

In the method of producing a piceatannol-containing composition according to the present invention, the extraction can be performed in a stepwise manner with a plurality of solvents. This can produce a piceatannol-containing composition containing piceatannol at a high content at a higher yield.

Specifically, for example, passion fruit seeds are pulverized, any one of the above-mentioned aqueous alcohol-based solvent and the above-mentioned aqueous ketone-based solvent is added thereto, and the mixture is stirred to extract piceatannol into the solvent, to thereby obtain the first extract. Centrifugation or the like is performed to separate the extract and the residue not collected as the extract, and the other not selected out of the above-mentioned solvents is added to the residue, and the mixture is stirred to extract piceatannol into the solvent, to thereby obtain the second extract. Then, the first extract and second extract are mixed. It should be noted that, needless to say, the second extract can be utilized alone as the passion fruit seed extract.

Further, if the passion fruit seeds are subjected to the first extraction treatment with the above-mentioned aqueous alcohol-based solvent or the above-mentioned aqueous ketone-based solvent, the property such as texture is considered to change into one preferred for the extraction. Therefore, the subsequent second extraction treatment can be expected to improve the extraction efficiency not only in the case of using the above-mentioned aqueous alcohol-based solvent or the above-mentioned aqueous ketone-based solvent but also in the case of using another solvent. Moreover, as shown in Examples below, high extraction efficiency in the case of using the above-mentioned aqueous alcohol-based solvent or the above-mentioned aqueous ketone-based solvent is considered to be provided by water contained in the solvent. Accordingly, if the passion fruit seeds are subjected to the first extraction treatment with water or an aqueous solvent, the subsequent second extraction treatment can be expected to improve the extraction efficiency not only in the case of using the above-mentioned aqueous alcohol-based solvent or the above-mentioned aqueous ketone-based solvent but also in the case of using another solvent.

The passion fruit seed extract obtained by the above-mentioned method can be used to prepare a piceatannol-containing composition in a liquid form without further treatments or after concentration. The extract may be further powderized by freeze-drying or spray-drying to prepare a piceatannol-containing composition in a powder form. The form of the extract is not limited to these forms. Insoluble matter contained in the extract can be appropriately removed by filtration or the like. The insoluble matter may further be pulverized into fine particles.

Further, the primary extract from the passion fruit seeds obtained as described above may be fractionated and purified based on piceatannol as an index by ion exchange, size exclusion column chromatography, HPLC, gel filtration, membrane separation, or the like to prepare the piceatannol-containing composition.

Specifically, for example, as shown in Examples below, when the composition extracted from the passion fruit seeds is subjected to HPLC under the following conditions, piceatannol is eluted at about 41 minutes. Meanwhile, when the eluted fraction is subjected to mass spectrometry using a mass spectrometer, a signal of negative ion mode is exhibited at m/z 243.

[HPLC Conditions]
  Column: Mightysil RP-18 GP 150-4.6, diameter: 4.6 mm, length: 150 mm (manufactured by KANTO CHEMICAL CO., INC.)
  Column temperature: 40° C.
  Elution conditions: flow rate: 1 ml/min, 0% methanol-30% methanol (60 min)
  UV detection: 280 nm Therefore, in the present invention, it is possible to prepare a piceatannol-containing composition, which is derived from passion fruit seeds and has an increased piceatannol content, by appropriately performing fractionation and purification based on piceatannol physical properties exemplified above as indices.

If necessary, the piceatannol-containing composition of the present invention may be supplemented with a pharmaceutically acceptable base or carrier and used as a drug in a form of a tablet, a granulated drug, a powdered drug, a liquid, a powder, a granule, a capsule, a jelly, or the like, or may be used as a cosmetic in a form of an ointment, a cream, a gel, a pack, a lotion, a cosmetic preparation, or the like.

Meanwhile, the piceatannol-containing composition of the present invention may be blended in food for specified health use, a dietary supplement, a functional food, or the like before ingestion. Examples of the foods include: confectionery such as a chocolate, a biscuit, a gum, a candy, a cookie, a gummi candy, or tableted confectionery; a cereal; a beverage such as a powder beverage, a soft drink, a milk beverage, a nutritional beverage, a carbonated drink, and a jelly drink; and a frozen dessert such as an ice cream or a sherbet. Moreover, preferred examples thereof include a noodle such as soba, pasta, udon, and somen. In the cases of the food for specified health use, dietary supplement, and the like, the composition may have a form of a powder, a granule, a capsule, a syrup, a tablet, or a sugar-coated tablet.

EXAMPLE

Hereinafter, the present invention is described specifically by way of examples, but the scope of the present invention is not limited by the examples.

Test Example 1

Detection and Identification of Piceatannol from Passion Fruit

Passion fruit was divided into three parts of pericarp, sarcocarp, and seeds, and the parts were separately freeze-dried and pulverized by a pulverizer (product name "Sample mill type SK-M," manufactured by KYORITSU RIKO K.K.), followed by extraction of the respective parts with 80% aqueous ethanol. The resultant products were centrifuged, the supernatants were then separated and concentrated by evaporation, and the concentrates were freeze-dried to obtain powders. The powders were dissolved in water to obtain extracts. Then, the seed extract, the pericarp extract, and the sarcocarp extract were diluted so that the concentrations in terms of solid content were 0.01 g/ml, 0.1 g/ml, and 0.1 g/ml, respectively, and 5 µl each of the extracts were subjected to HPLC.

Figure 1B:
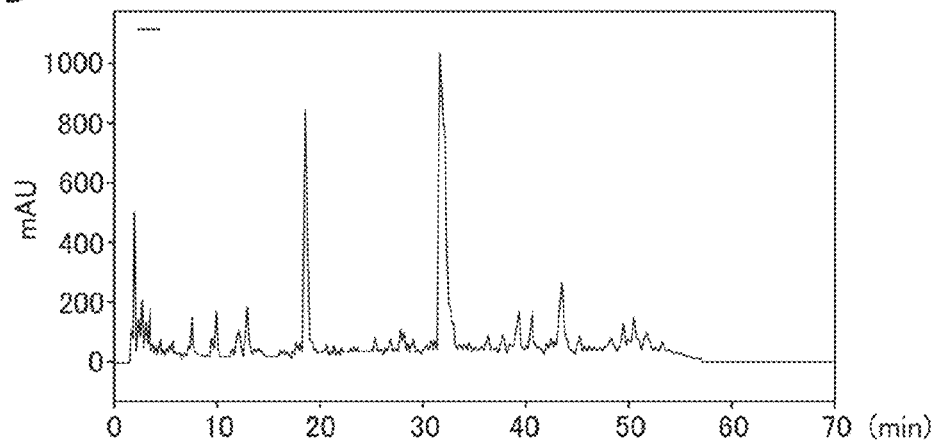
Figure 1C:
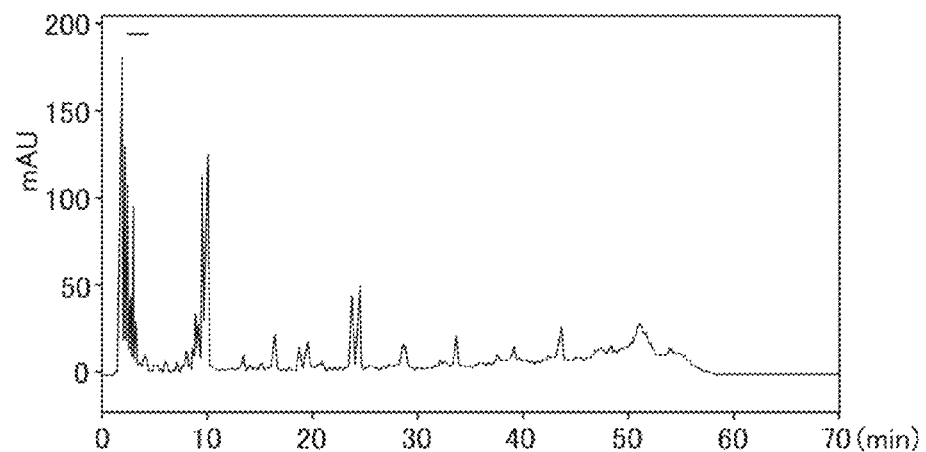

Analysis conditions for HPLC were as described below.
Column: Mightysil RP-18 GP 150-4.6, diameter: 4.6 mm, length: 150 mm (manufactured by KANTO CHEMICAL CO., INC.)
Column temperature: 40° C.
Elution conditions: flow rate: 1 ml/min, 0% methanol-30% methanol (60 min)
UV detection: 280 nm FIGS. 1A to 1C show HPLC chromatograms of the above-mentioned respective extracts. As a result, as shown in FIG. 1A, in the case of the seed extract, a peak was detected at about 41 minutes. On the other hand, in the cases of the pericarp extract and the sarcocarp extract, the peak at about 41 minutes was not able to be detected although the concentration in terms of solid content according to the injection was 10 times larger than that of the seed extract.

Subsequently, the characteristics of the component contained in the seed extract and eluted at the retention time of about 41 minutes described above were identified as described below.

Figure 2B:
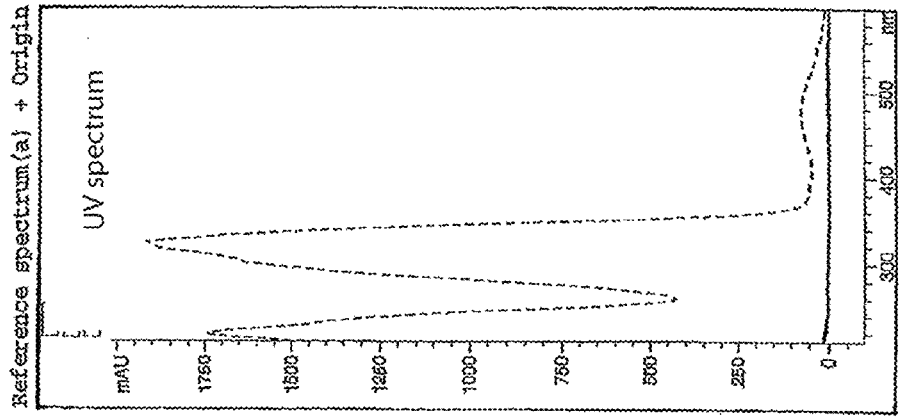
FIG. 2 Diagrams showing a mass spectrum (A) and a UV spectrum (B) of a component eluted at about 41 minutes in HPLC analysis of FIG. 1.
Figure 2A:
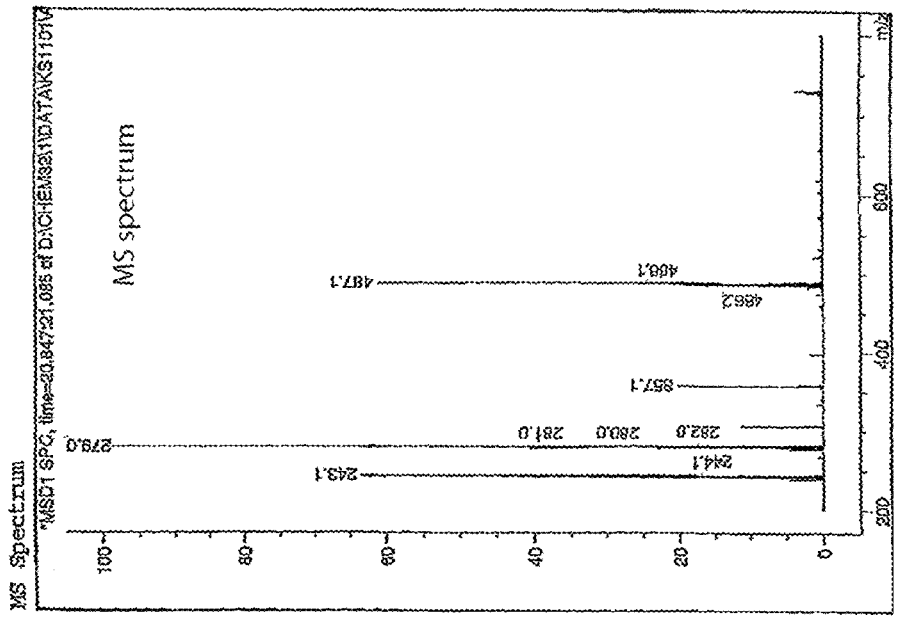

First, a mass spectrum of the component was measured using an HPLC/mass spectrometer (manufactured by THERMO ELECTRON Co., Ltd., device name "Thermo-LCQ-MS/MS") (FIG. 2A). Although the measurement was performed in both positive and negative ion modes, a preferred ion was found in the negative mode, and hence the data was used. As a result, a major signal at m/z 243 was (M-H)⁻, and the other peaks at m/z 279 and m/z 487 were able to be attributed to (M+2H₂O—H)⁻ and (M×2-H)⁻, respectively. Therefore, the molecular weight was able to be determined as 244. Further, when a UV spectrum of the component was measured, 220 nm, 304 nm, and 322 nm were observed as $\lambda_{max}$ (FIG. 2B).

Figure 3A:
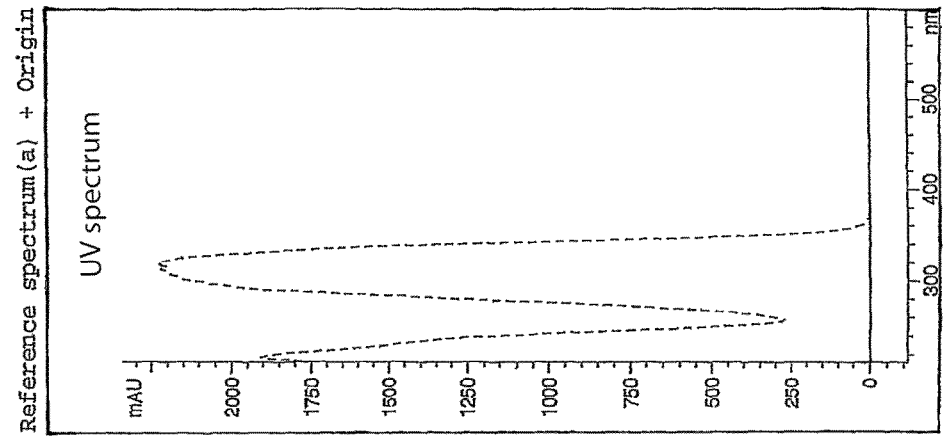
FIG. 3 Diagrams showing a mass spectrum (A) and a UV spectrum (B) of resveratrol (molecular weight: 228).
Figure 3B:
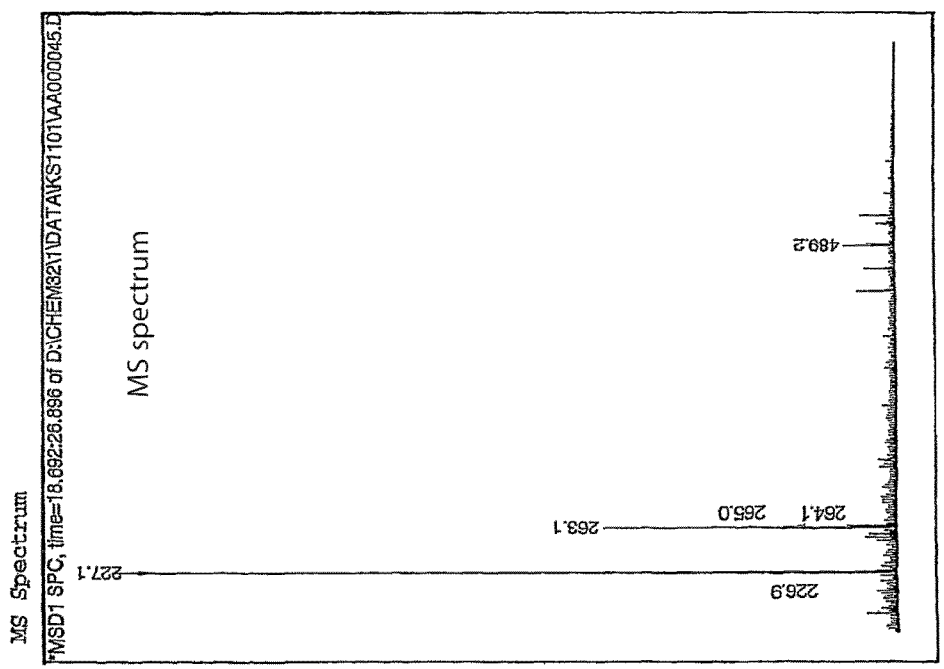

The results of the mass spectrometry and the UV spectrometry were found to be similar to those of resveratrol (molecular weight: 228), which is a polyphenol contained in peanut pericarp (see FIGS. 3A and 3B). In addition, adsorption to polyvinylpolypyrrolidone (PVPP), which was a resin capable of adsorbing a polyphenol, was also confirmed separately. Moreover, the peak at about 41 minutes was found to have a short retention time to a reverse-phase column compared with the retention time of resveratrol under the same HPLC conditions. All the results suggest that the component contained in the above-mentioned seed extract and eluted at the retention time of 41 minutes is piceatannol (molecular weight: 244), which is represented by the following formula (1) and has a molecular weight larger than that of resveratrol by one hydroxy group.

[Chem. 2]

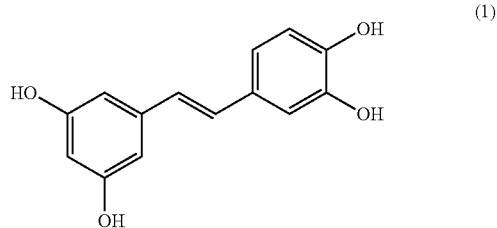

(1)

Figure 4B:
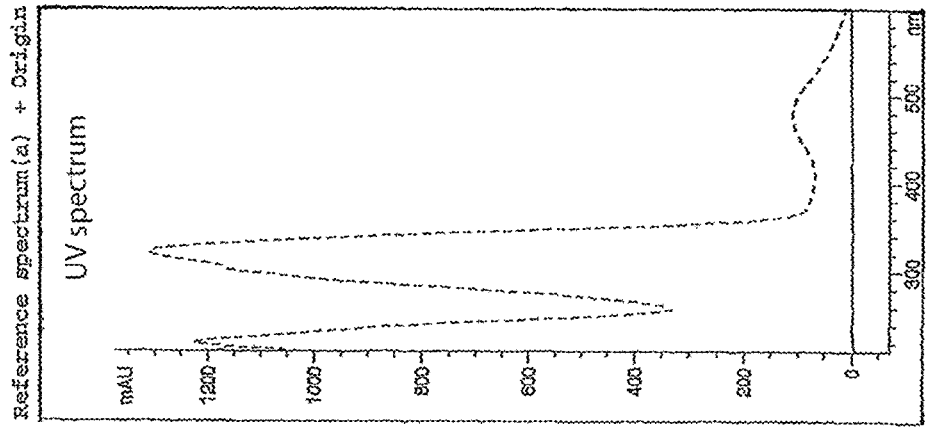
FIG. 4 Diagrams showing a mass spectrum (A) and a UV spectrum (B) of piceatannol (molecular weight: 244).
Figure 4A:
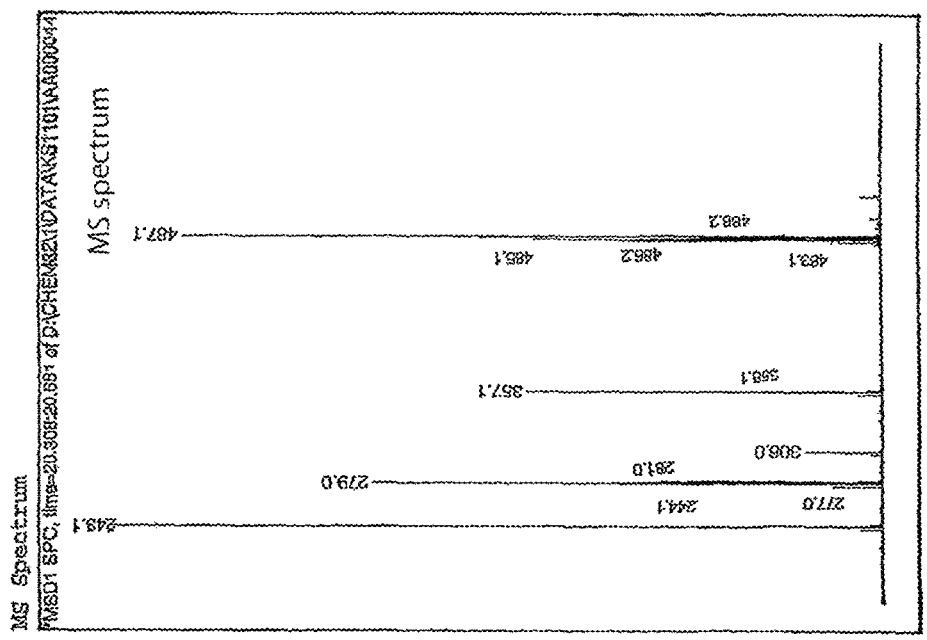

Then, a pure compound of piceatannol (manufactured by Sigma-Aldrich Corporation) was analyzed by HPLC under the same conditions as described above to further provide a mass spectrum and a UV spectrum (FIGS. 4A and 4B). The results show that all of the retention times of HPLC and attributions of the mass spectrum and UV spectrum correspond to the above-mentioned ones.

This reveals that the peak at about 41 minutes in the above-mentioned HPLC analysis for the above-mentioned seed extract is a peak of piceatannol, and the passion fruit seeds contain a large amount of piceatannol. On the other hand, piceatannol was not detected from any of the pericarp and sarcocarp of the passion fruit.

Test Example 2

Extraction of Piceatannol from Passion Fruit Seeds (1)

A method of extracting piceatannol from passion fruit seeds was examined. Specifically, extraction efficiencies of two kinds of passion fruit seeds (domestic and foreign-grown) were determined using different solvents.

(1) Extraction with 80% Aqueous Ethanol

To 5 g of pulverized seeds were added 50 ml of 80% aqueous ethanol, and extraction was performed by ultrasonication for 30 minutes. The supernatant was collected, and extraction was further performed twice (three times in total) by the same procedures. The collected extracts were combined, and the volume of the resultant extract was adjusted to 200 ml with 80% aqueous ethanol, and 10 µl of the solution were subjected to HPLC. Then, according to a conventional method, piceatannol contained in the extract was quantified by assigning an area under the peak of the HPLC analysis to a calibration curve based on concentrations of a standard. It should be noted that resveratrol was also quantified for reference in the same way as described above.

(2) Extraction with 70% Aqueous Acetone

To the extraction residue obtained after the extraction with 80% aqueous ethanol described above were added 50 ml of 70% aqueous acetone, and extraction was performed by ultrasonication for 30 minutes. The supernatant was collected, and extraction was further performed twice (three times in total) by the same procedures. The collected extracts were combined, and the volume of the resultant extract was adjusted to 200 ml with 70% aqueous acetone, followed by quantification of piceatannol and resveratrol contained in the extract in the same way as described above.

(3) Extraction with Ethyl Acetate

Extraction was performed for seeds of (the above-mentioned foreign-grown) passion fruit in the same way as in the case of the extraction with 80% aqueous ethanol except that ethyl acetate was used as the solvent, and piceatannol and resveratrol extracted from 5 g of freeze-dried seed powder were quantified.

(4) Extraction with Dichloromethane

Extraction was performed for seeds of (the above-mentioned foreign-grown) passion fruit in the same way as in the case of the extraction with 80% aqueous ethanol except that dichloromethane was used as the solvent, and piceatannol and resveratrol extracted from 5 g of freeze-dried seed powder were quantified.

The results are collectively shown in Table 1. It should be noted that Table 1 shows values obtained by converting the results of the extraction efficiencies into amounts of piceatannol and resveratrol extracted from 100 g of freeze-dried seed powder.

TABLE 1

| | Extracted piceatannol (mg) converted into amount per 100 g of freeze-dried seeds | | | | | | | |
|---|---|---|---|---|---|---|---|---|
| | Passion fruit sample 1 (domestic) | | | Passion fruit sample 2 (foreign-grown) | | | | |
| | Extraction solvent | | | | | | | |
| | 80% aqueous ethanol (A) | 70% aqueous acetone (B) | Total (A + B) | 80% aqueous ethanol (A) | 70% aqueous acetone (B) | Total (A + B) | Ethyl acetate | Dichloromethane |
| Piceatannol | 63 | 280 | 343 | 65 | 255 | 320 | 14.3 | Not detectable |
| Resveratrol (reference) | 5 | 10 | 15 | 3 | 15 | 18 | 0.6 | Not detectable |

As shown in Table 1, even from the extraction residue obtained after the extraction with 80% aqueous ethanol, piceatannol was extracted in an amount larger than that in the case of the extraction with 80% aqueous ethanol. On the other hand, in the case of the extraction with ethyl acetate alone, the extraction efficiency was low, while in the case of the extraction with dichloromethane alone, piceatannol and resveratrol were not detectable. Therefore, it was clarified that the extraction with 70% aqueous acetone provided the highest efficiency. Moreover, it was clarified that a combination of the extraction with 80% aqueous ethanol and the extraction with 70% aqueous acetone was found to provide still higher extraction efficiency.

Test Example 3

Extraction of Piceatannol from Passion Fruit Seeds (2)

The method of extracting piceatannol from passion fruit seeds was further examined. Specifically, an effect of a water content of ethanol or acetone as a solvent on the extraction efficiency was investigated.

To investigate the effect, piceatannol and resveratrol extracted from 5 g of freeze-dried seed powder of (the above-mentioned foreign-grown) passion fruit were quantified using ethanol or acetone with different water contents as the solvent in the same way as in Test Example 2. It should be noted that any of the solvents used in Test Example 2 above, ethyl acetate and dichloromethane, has poor compatibility with water, and hence it is impossible to prepare solvents with the same water contents.

Figure 5A:
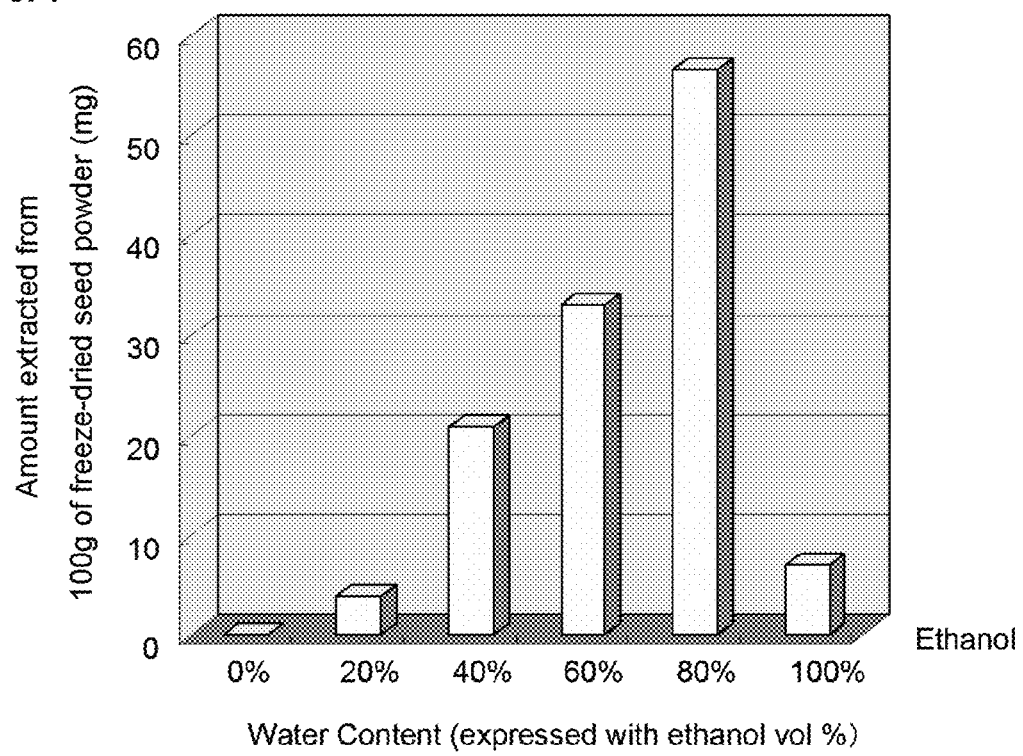
FIG. 5 Diagrams each showing an effect of a water content of ethanol (A) or acetone (B) as a solvent on extraction efficiency of piceatannol.
Figure 5B:
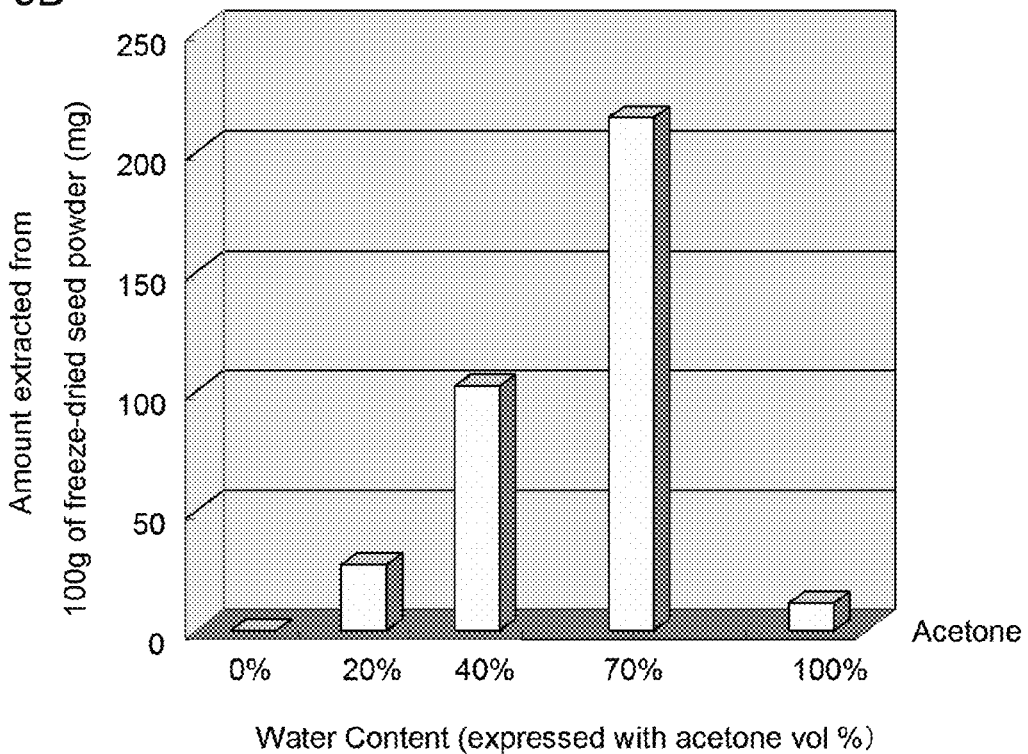

The results are collectively shown in Table 2 below. Further, the results of the piceatannol are shown as a graph in FIG. 5. It should be noted that Table 2 and FIG. 5 show values obtained by converting the results of the extraction efficiencies into amounts of piceatannol and resveratrol extracted from 100 g of freeze-dried seed powder.

TABLE 2

Extracted piceatannol (mg) converted into amount per 100 g of freeze-dried seeds

| Ethanol | | | Acetone | | |
|---|---|---|---|---|---|
| Water content (represented as vol % of ethanol) | Piceatannol | Resveratrol | Water content (represented as vol % of acetone) | Piceatannol | Resveratrol |
| 0 | Not detectable | Not detectable | 0 | Not detectable | Not detectable |
| 20 | 3.8 | 0.6 | 20 | 27.5 | 0.8 |
| 40 | 20.8 | 0.8 | 40 | 101.5 | 3.0 |
| 60 | 33.0 | 1.5 | 70 | 214.4 | 7.2 |
| 80 | 56.5 | 2.2 | * | * | * |
| 100 | 7.0 | 1.1 | 100 | 10.7 | 1.0 |

*: No data

As shown in Table 2 and FIG. 5, in the case of using ethanol, the extraction with 80% aqueous ethanol provided the highest efficiency. Meanwhile, in the case of using acetone, the extraction with 70% aqueous acetone provided the highest efficiency.

Test Example 4

Extracts obtained after removal of the solvents in Test Example 2 above (derived from the foreign-grown passion fruit) were weighed to calculate the piceatannol contents in terms of solid content. Table 3 shows the resultant values.

TABLE 3

| Extraction solvent | 80% aqueous ethanol | 70% aqueous acetone |
|---|---|---|
| Piceatannol content (mass %) in terms of solid content in extract | 2.6 | 3.7 |

As shown in Table 3, in the case of the extraction with 80% aqueous ethanol, the piceatannol concentration in terms of solid content was found to be 2.6 mg/100 mg of the extract (2.6 mass %). Meanwhile, in the case of the extraction with 70% aqueous acetone after the extraction with 80% aqueous ethanol, the piceatannol concentration in terms of solid content was found to be 3.7 mg/100 mg of the extract (3.7 mass %). Therefore, it was clarified that the extraction with 70% aqueous acetone was able to give a larger amount of piceatannol (as shown in Test Examples 2 and 3) and a higher piceatannol purity.

The invention claimed is:

1. An aqueous alcohol-based or ketone-based piceatannol-containing extractant composition, wherein the piceatannol-containing extractant composition is obtained by aqueous alcohol-based or ketone-based extraction from passion fruit seed and contains piceatannol at a content of 0.1 to 50 mass % in terms of solid content, and wherein the aqueous alcohol-based piceatannol-containing extractant composition contains 20 to 80% alcohol and the aqueous ketone-based piceatannol-containing extractant composition contains 20 to 70% ketone.

2. An aqueous alcohol-based or ketone-based piceatannol-containing extractant composition as claimed in claim 1, wherein the piceatannol content is 2.6 to 50 mass % in terms of solid content.

3. A cosmetic, wherein the cosmetic has added thereto a piceatannol-containing extractant composition, wherein the piceatannol-containing extractant composition is obtained by an aqueous alcohol-based or ketone-based extraction from passion fruit seed and contains piceatannol at a content of 0.1 to 99.9 mass % in terms of solid content, and wherein the cosmetic is in the form of an ointment, cream, or lotion.

4. A cosmetic, according to claim 3, wherein the piceatannol content is 2.6 to 99.9 mass % in terms of solid content.

* * * * *